April 20, 1954 O. E. McGUIRE Plant Pat. 1,271
POTHOS PLANT
Filed May 4, 1953
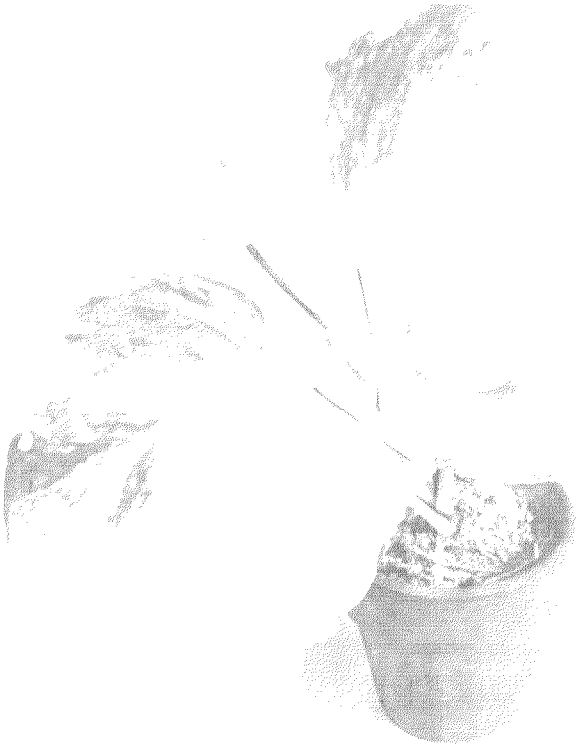
INVENTOR
ORVID E. McGUIRE
BY Wyatt Donnell
ATTORNEY Patented Apr. 20, 1954

Plant Pat. 1,271

UNITED STATES PATENT OFFICE 1,271

POTHOS PLANT

Orvid E. McGuire, Apopka, Fla., assignor to The Evergreen Gardens, Apopka, Fla.

Application May 4, 1953, Serial No. 353,030

1 Claim. (Cl. 47—59)

The present invention relates to a new and distinct variety of Pothos plant which originated as a sport of the variety *Pothos areus*.

The new variety was discovered by me in my greenhouse as a sport on the parent plant when the sport only had two leaves. After observing its growth I removed the tip, taking the aerial roots, in order to insure the possibility of asexual propagation. After tipping the plant several times, I began asexual propagation by taking a portion of the stem with a leaf and an eye, which is the faster means of propagation. The plant has been asexually reproduced through several generations in my greenhouse in Apopka, Florida, its characteristics remaining constant through the many thousands of specimens produced.

The representation on the drawing is a perspective of the plant, taken slightly from above, which illustrates its manner of growth and particularly the characteristic color and color pattern of the leaves.

The plant is distinguished from its parent and from other varieties of Pothos particularly by its variegated color, the leaves being mottled with distinct shades of white, green, and yellow, the basic or predominant color being white. The plant has cordate-ovate-acute leaves. The leaves of the parent plant are predominantly dark green with occasional blotches of light yellow, a substantial percentage of the leaves of the parent being entirely green without any yellow.

The white portion of the leaves varies from "Pure White," Plate 1, to "Creamy White," Plate 2 (Koster's Color Guide, copyright 1931, by A. T. De La Mere Co., Inc., New York, New York). Some portions of the leaves have green and yellow shades overlying or combining to produce a misty "Yellowish Green," Plate 73 (Koster's Color Guide), or "Chartreuse Green," Plates 663, 663/1, 663/2, page 90 (Horticulture Colour Chart, issued by The British Colour Council in collaboration with the Royal Horticultural Society, copyright 1938, by Robert F. Wilson). The dark green or substantially solid green portions of the leaves are similar to "Boxwood Green," Plate 79 (Koster's Color Guide), although somewhat darker. The yellow color in the leaves is a delicate hue somewhat lighter than "Sulphur Yellow," Plate 5 (Koster's Color Guide), or "Sulphur Yellow," Plate 1/2, page 1 (Horticultural Colour Chart), although it is usually interspersed with white and green. The colors designated are believed to be approximations to the indicated standards, although not necessarily identical therewith.

The underside of the leaves corresponds in color and mottling to the upper side except that the underside is less distinct and of a somewhat lighter shade.

The stems are yellowish white with irregular streaks of green. The leaves vary from approximately two and one-half inches to three inches in width, and from three and one-half inches to four inches in length, depending on the growing conditions. The petioles of the leaves range from one and one-half inches to two inches in length and are concave with a sheath on the outer edge which withers and dies, falling from the petiole as the plant grows. The buds are long and slender and occur singularly closely along the stem at the base of the uppermost leaf, and the end of the stem, the sheath enclosing the new growing stem, leaf, and petiole.

The plant is a strong climber and tends to have smaller leaves as it grows trailing down, although when grown upright on a support, the leaves increase in size as it grows, to an abnormally large size. The plant sends out aerial roots from the stem nodes which cling to whatever the plant is growing on. The roots are usually fibrous and cord-like when growing upwardly. When the stem grows upright, the petiole leaves the stem at approximately a 90° angle. When the plant is growing down, however, the leaves turn upward to the light.

The plant grows a little faster than other varieties of variegated Pothos and almost as fast as the parent. It appears to thrive best at a temperature of 70 to 85° F. in the greenhouse with sixty-five to seventy-five per cent shade. The plant will also grow outside under suitable shelter and can survive a temperature of 33° F. for a few hours, depending on the condition of the plant.

The plant is particularly distinguishable from other variegated Pothos such as *Pothos Wilcoxii*, the latter being green and yellow with green being predominant; also from the Pothos Marble Queen which is green and white, the predominant color being green; or from the Silver Marble Pothos which is white and green with the predominant color being white. The named varieties are unpatented to my knowledge.

Having thus disclosed by discovery, I claim:

The new and distinct Pothos plant disclosed, characterized by the variegated mottling of its leaves with white, green, and yellow, white being predominant.

No references cited.